United States Patent
Gogolewski et al.

(10) Patent No.: US 8,097,266 B2
(45) Date of Patent: Jan. 17, 2012

(54) SOLVENT SYSTEMS FOR POUR-ON FORMULATIONS FOR COMBATING PARASITES

(75) Inventors: Ronald Peter Gogolewski, Casula (AU); Douglas Cleverly, Karaka Papakura (NZ); Paul Thwaites, Toms River, NJ (US); Mark David Soll, Alpharetta, GA (US)

(73) Assignee: Merial Limited, Duluth, GA (US)

( * ) Notice: Subject to any disclaimer, the term of this patent is extended or adjusted under 35 U.S.C. 154(b) by 467 days.

(21) Appl. No.: 12/324,066

(22) Filed: Nov. 26, 2008

(65) Prior Publication Data

US 2009/0163575 A1 Jun. 25, 2009

Related U.S. Application Data

(60) Provisional application No. 60/990,205, filed on Nov. 26, 2007.

(51) Int. Cl.
*A01N 25/02* (2006.01)
(52) U.S. Cl. ............ 424/405; 424/406; 514/30; 514/603
(58) Field of Classification Search .................. None
See application file for complete search history.

(56) References Cited

U.S. PATENT DOCUMENTS

| | | | |
|---|---|---|---|
| 5,773,422 A | 6/1998 | Komer | |
| 6,991,801 B2 | 1/2006 | Soll et al. | |
| 7,531,186 B2 * | 5/2009 | Boeckh et al. | 424/406 |
| 2002/0037863 A1 | 3/2002 | Geary | |
| 2004/0077703 A1 * | 4/2004 | Soll et al. | 514/410 |
| 2005/0137244 A1 * | 6/2005 | Boeckh et al. | 514/406 |
| 2007/0042013 A1 * | 2/2007 | Soll et al. | 424/405 |
| 2008/0003282 A1 * | 1/2008 | Soll et al. | 424/464 |
| 2008/0312272 A1 * | 12/2008 | Soll et al. | 514/303 |
| 2009/0192207 A1 * | 7/2009 | Boeckh et al. | 514/406 |
| 2010/0125097 A1 * | 5/2010 | Soll et al. | 514/407 |

\* cited by examiner

*Primary Examiner* — Neil Levy
(74) *Attorney, Agent, or Firm* — Judy Jarecki-Black; Chad Kitchen; Merial Limited

(57) ABSTRACT

This invention relates to pharmaceutical and veterinary formulations providing enhanced solvency and stability for pharmaceutical and veterinary agents for administration to animals, especially ruminants. In addition, the invention relates to pour-on formulations for combating parasites in animals, such as cattle and sheep. In some embodiments, this invention provides glycol-ether-based pour-on formulations comprising a composition comprising a flukicide, such as, for example, clorsulon (4-amino-6-trichloroethenyl-1,3-benzene disulfonamide) and/or a macrolide anthelmintic or antiparasitic agent. In other embodiments, the invention provides pour-on formulations comprising at least one active agent, a glycol ether, and a stability enhancer. This invention also provides for methods for eradicating, controlling, and/or preventing parasite infestation in animals, such as cattle and sheep.

4 Claims, 11 Drawing Sheets

Figure 1. Analytical Data for Ivermectin and Clorsulon Formulations for Pharmacokinetic / Efficacy Study

| Formulation 1 | | | |
|---|---|---|---|
| BATCH SIZE: 1 Liter | | | |
| PARAMETER | SPECIFICATION | METHOD | RESULT |
| Appearance | Clear, straw yellow liquid, free from any extraneous matter | Visual | Clear, straw yellow liquid, free from any extraneous matter |
| Clorsulon Assay | 16.6 – 18.4%w/v | As described in Example 2 | 17.4%w/v |
| Ivermectin Assay | 0.475 – 0.525%w/v | As described in Example 2 | 0.496%w/v |
| Specific Gravity (@ 20°C) | 1.045 – 1.065 | Pyknometer | 1.051 |

Figure 1 (continued).

| Formulation 2 | | | |
|---|---|---|---|
| BATCH SIZE: 1 Liter | | | |
| PARAMETER | SPECIFICATION | METHOD | RESULT |
| Appearance | Clear, straw yellow liquid, free from any extraneous matter | Visual | Clear, straw yellow liquid, free from any extraneous matter |
| Clorsulon Assay | 16.6 – 18.4%w/v | As described in Example 2 | 17.5%w/v |
| Ivermectin Assay | 0.475 – 0.525%w/v | As described in Example 2 | 0.500%w/v |
| Specific Gravity (@ 20°C) | 1.025 – 1.045 | Pyknometer | 1.030 |

Figure 1 (continued).

| Formulation 3 | | | |
|---|---|---|---|
| BATCH SIZE: 1 Liter | | | |
| PARAMETER | SPECIFICATION | METHOD | RESULT |
| Appearance | Clear, straw yellow liquid, free from any extraneous matter | Visual | Clear, straw yellow liquid, free from any extraneous matter |
| Clorsulon Assay | 16.6 – 18.4%w/v | As described in Example 2 | 17.2%w/v |
| Ivermectin Assay | 0.475 – 0.525%w/v | As described in Example 2 | 0.500%w/v |
| Specific Gravity (@ 20°C) | 0.965 – 0.985 | Pyknometer | 0.970 |

Figure 6. Plasma Eprinomectin
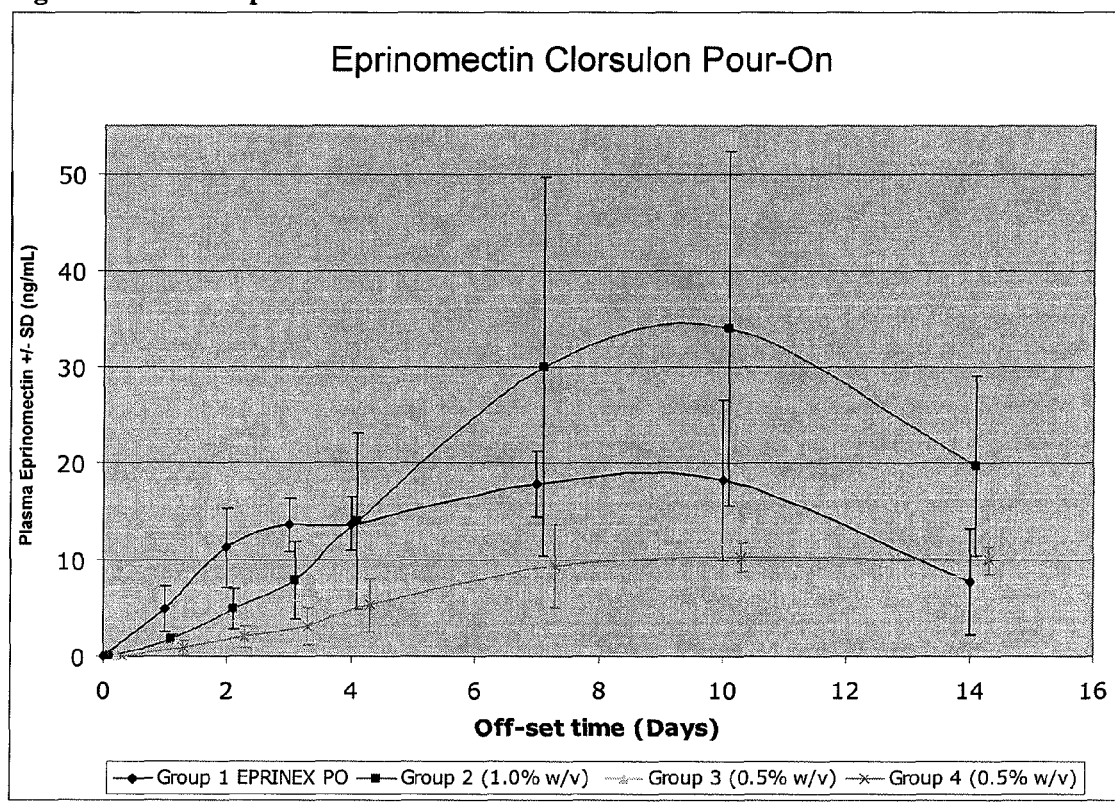

Figure 7. Observed Estimated Mean Area Under the Curve Mean Plasma Eprinomectin
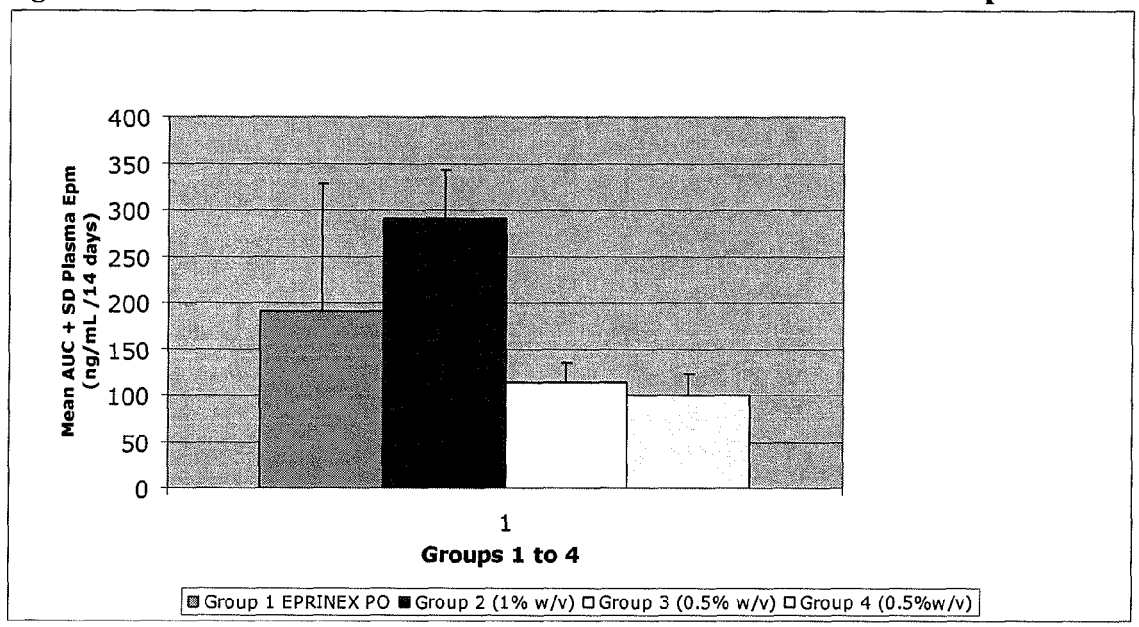

Figure 8. Group 2 Mean Eprinomectin Plasma Concentration
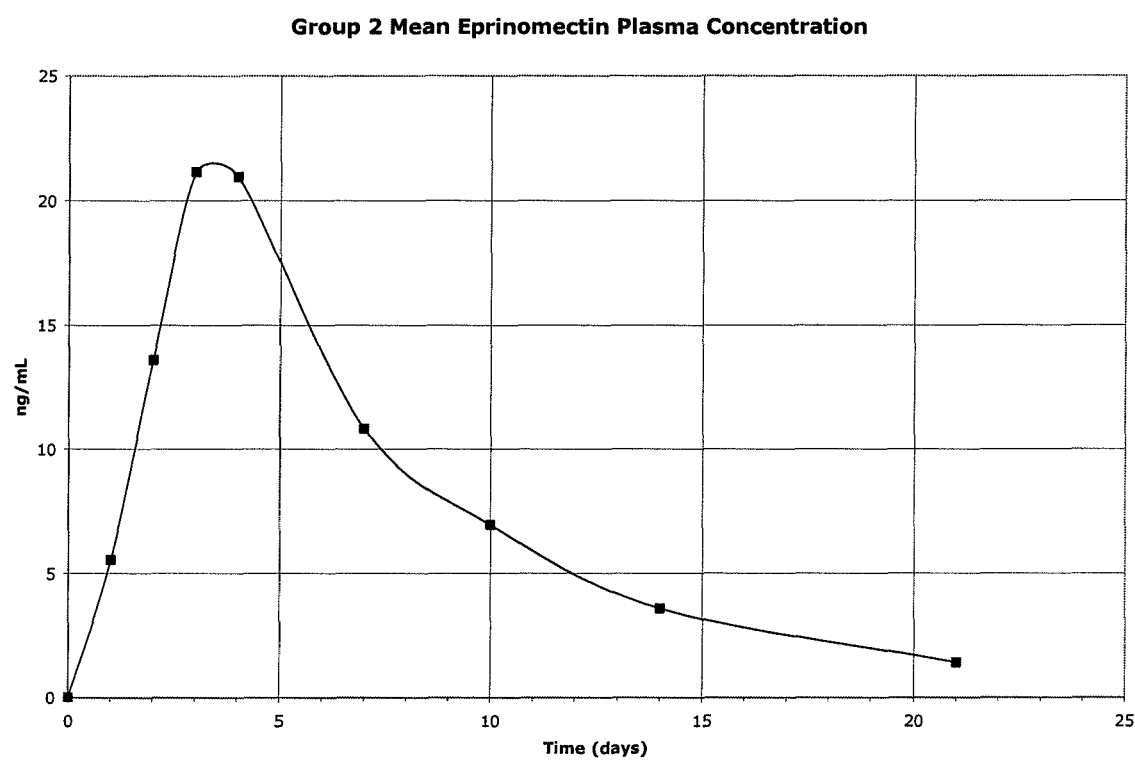

Figure 9. Group 2 Mean Clorsulon Plasma Concentration
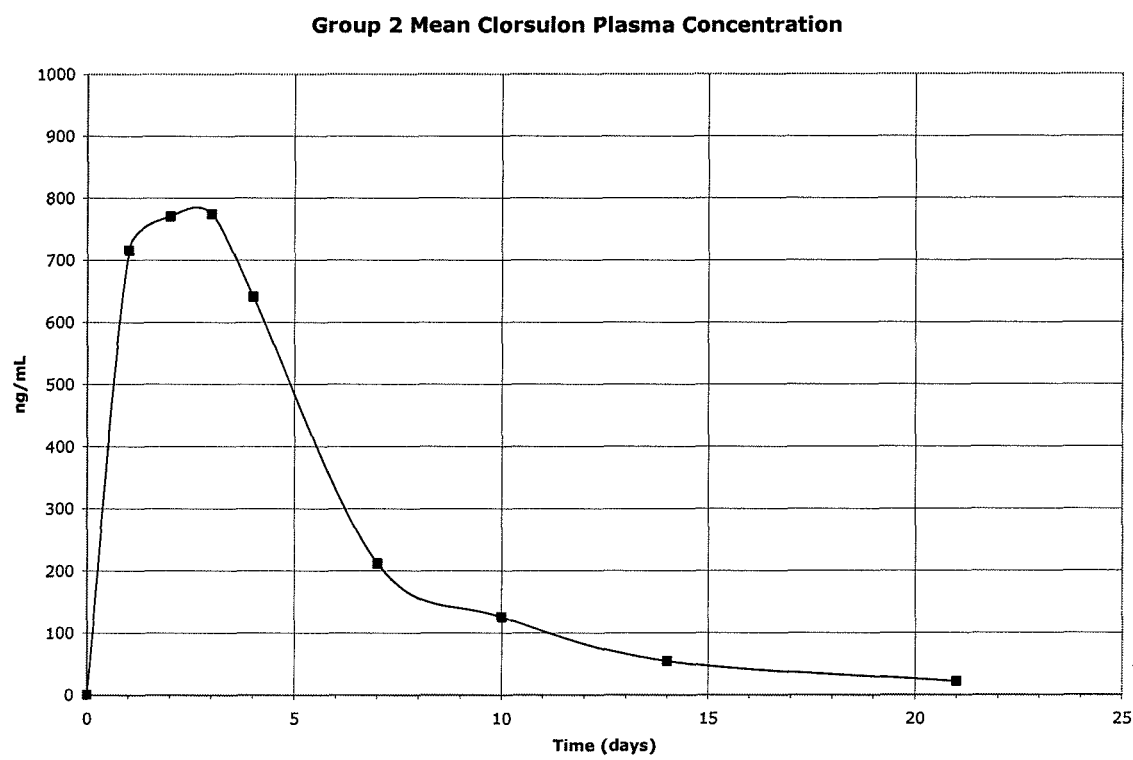

SOLVENT SYSTEMS FOR POUR-ON FORMULATIONS FOR COMBATING PARASITES

CROSS-REFERENCE TO RELATED APPLICATIONS

This application claims the benefit of priority of U.S. Provisional Application Ser. No. 60/990,205 filed Nov. 26, 2007, which is hereby incorporated by reference in its entirety. Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

FIELD OF THE INVENTION

This invention relates to pharmaceutical and veterinary formulations providing enhanced solvency, stability and/or transdermal absorption for pharmaceutical and veterinary agents for administration to animals, especially ruminants. In addition, the invention relates to pour-on formulations for combating parasites in animals, such as cattle and sheep. In some embodiments, the formulations of the invention comprise a solvent that spreads over the applied surface to provide enhanced absorption of a pharmaceutical or veterinary agent. In some embodiments, this invention provides glycol-ether-based pour-on formulations comprising a composition comprising a flukicide, such as, for example, clorsulon (4-amino-6-trichloroethenyl-1,3-benzene disulfonamide) and/or a macrolide anthelmintic or other antiparasitic agent. In other embodiments, the invention provides pour-on formulations comprising at least one active agent, a glycol ether, and a stability enhancer. This invention also provides for methods for eradicating, controlling, and/or preventing parasite infestation in animals, such as cattle and sheep.

BACKGROUND OF THE INVENTION

Animals such as mammals and birds are often susceptible to parasite infestations. These parasites may be ectoparasites, such as insects, and endoparasites such as filariae and worms.

Farm animals are particularly susceptible to parasite infestations, which can be associated with illness and death or reduced productivity. For example, cattle are affected by a large number of parasites. An example includes the parasitic trematode, *Fasciola hepatica* or common liver fluke. *F. hepatica* is an important trematode of domestic ruminants and is the most common cause of liver fluke disease in temperate areas of the world. Migration of flukes in the liver damages the tissue, resulting in formation of scar tissue, disrupting normal liver function and decreasing albumin production. Flukes also ingest red blood cells directly, causing iron-deficiency anemia if the animal's iron stores are exhausted by replacing lost cells. The combination of these conditions over a prolonged period causes decreased growth, weight loss, anemia, and edema. Liveweight gain and milk production can be reduced by up to 8% in moderately infected cattle. Economically important infections are seen in cattle and sheep in three forms: chronic, which is rarely fatal in cattle but often fatal in sheep; subacute or acute, which is primarily in sheep and often fatal; and in conjunction with "black disease" (infectious necrotic hepatitis), which is most common in sheep and usually fatal.

Animals and humans also suffer from endoparasitical infections including, for example, helminthiasis which is most frequently caused by a group of parasitic worms described as nematodes or heartworms or roundworms. These parasites cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichuris, Enterobius, Ostertagia, Haemonchus, Trichostrogylus, Cooperia, Nematodirus, Chabertia, Oesophagostomum, Bunostomum* and parasites that are found in the blood or other tissues and organs such as filarial worms and the extra intestinal stages of *Strogyloides, Toxocara* and *Trichinella.*

Also, a parasite which is very prevalent among farm animals is a tick genus *Boophilus*, especially those of the species microplus (cattle tick), decoloratus and anulatus. Ticks, such as *Boophilus microplus*, are particularly difficult to control because they live in the pasture where the farm animals graze. Other important parasites of cattle and sheep are listed as follows:

myiases such as *Dermatobia hominis* (known as Berne in Brazil) and *Cochlyomia hominivorax* (greenbottle); sheep myiases such as *Lucilia sericata, Lucilia cuprina* (known as blowfly strike in Australia, New Zealand and South Africa). These are flies whose larva constitute the animal parasite;

flies proper, namely those whose adult constitutes the parasite, such as *Haematobia irritans* (horn fly);

lice such as *Linognathus vitulorum*, etc.; and mites such as *Sarcoptes scabiei* and *Psoroptes ovis.*

Likewise, domesticated animals, such as cats and dogs, are often infested with one or more of the following ectoparasites:

cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dermatobia* sp., *Cochlyomia* sp., and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents, agents which cause diseases in both humans and animals. Major diseases which are caused by ticks include borrelioses (Lyme disease caused by *Borrelia burgdorferi*), babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

The above list is not exhaustive and other ectoparasites are well known in the art to be harmful to animals and humans. These include, for example, migrating dipterous larvae.

Endectocidal compounds, which exhibit a degree of activity against a wide range of endoparasites, are known in the art. These compounds possess a macrocyclic lactone ring and are known in the art to be particularly effective against ectoparasites, including lice, blowflies, flies, mosquitoes, mites, migrating dipterous larvae, and ticks, as well as endoparasites, such as nematodes, heartworms and roundworms. Compounds of this group include avermectins, milbemycins, and derivatives of these compounds, for example, abamectin, doramectin, emamectin, eprinomectin, ivermectin, latidectin, lepimectin, milbemectin, moxidectin or selamectin. Such substances are described, for example, in U.S. Pat. Nos. 3,950,360; 4,199,569; 4,879,749; and 5,268,710.

While it is known in the art that it is sometimes possible to combine various parasiticides in order to broaden the antiparasitical spectrum, it is not possible to predict, a priori, which combinations will work for a particular animal or disease state. For this reason, the results of various combinations are not always successful and there is a need in the art for more effective formulations which may be easily administered to the animal and have the required solvency, stability and bioavailability. The effectiveness of formulations comprising flukicides, such as clorsulon, and macrolide lactone anthelmintic or parasitic agents, such as ivermectin and eprinomectin, against an endoparasite or an ectoparasite in a specific host is especially difficult to formulate because of the challenges in achieving the required solvency, stability and bioavailability.

Thus, there is a need in the art for antiparasitic formulations that meet the required solvency, stability and bioavailability of the parasiticides to be formulated therein.

Citation or identification of any document in this application is not an admission that such document is available as prior art to the present invention.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 is a table depicting analytical data for various clorsulon and ivermectin combination formulations.

FIG. 6 is a graph depicting eprinomectin plasma levels over time.

FIG. 7 is a graph depicting mean AUC mean plasma eprinomectin levels.

FIG. 8 is a graph depicting mean eprinomectin plasma concentrations in treated cattle.

FIG. 9 is a graph depicting mean clorsulon plasma concentrations in treated cattle.

SUMMARY OF THE INVENTION

Figure 2:
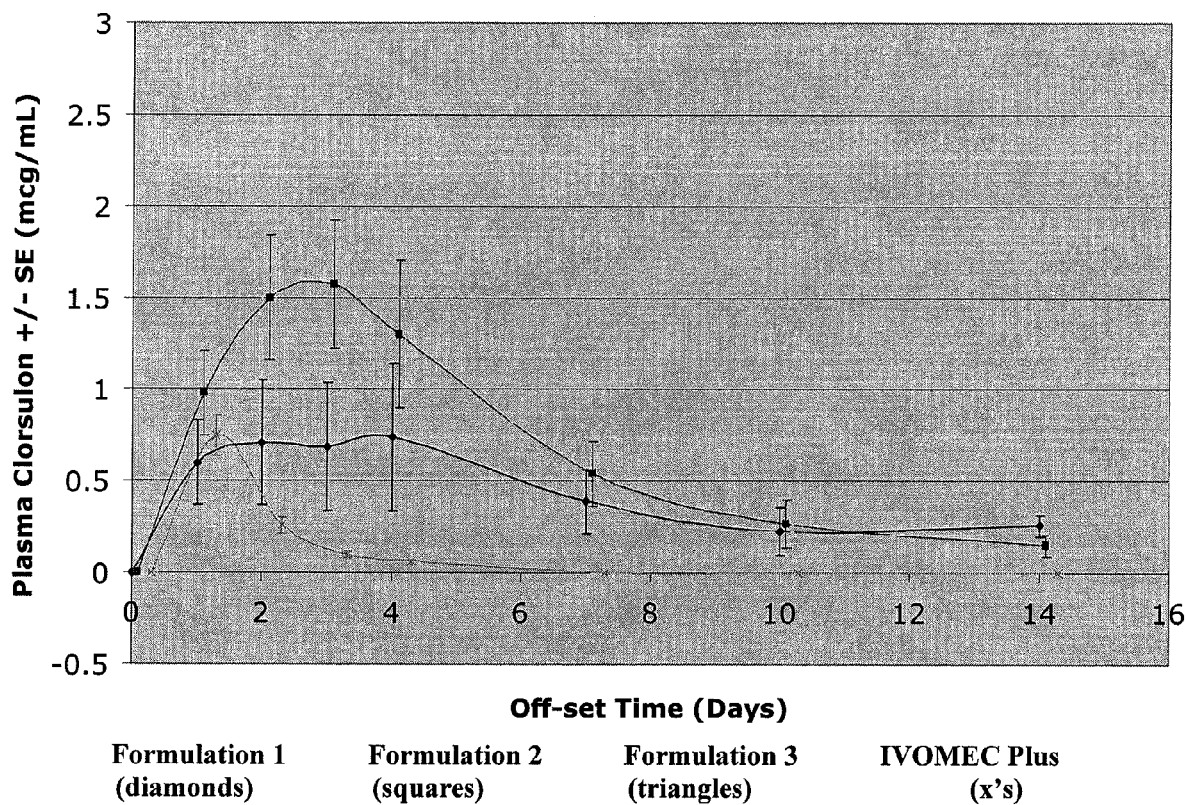
FIG. 2 is a graph depicting clorsulon plasma levels over time.

This invention relates to solvent systems that provide enhanced solvency, stability and bioavailability for active pharmaceutical or veterinary agents. In certain embodiments, the invention may provide a solvent system for a veterinary pour-on formulation for topical, transdermal treatment or prophylaxis of a parasiticidal infection, comprising (a) an effective amount of at least one active agent; (b) a glycol ether; and (c) a stability enhancer. Examples of stability enhancers suitable for use in the formulations of the invention include stabilized glycerol formal and polyethylene glycol (e.g., PEG 200). In certain embodiments, the stability enhancer is stabilized glycerol formal present in the formulation in an amount of about 5% w/v or less.

In certain embodiments, the glycol ether used in a formulation of the invention is selected from the group consisting of diethylene glycol monoethyl ether (also known as "Carbitol"), dipropylene glycol monomethyl ether (also known as methyl "Carbitol"), ethylene glycol monoethyl ether (also known as "Cellosolve"), ethylene glycol monomethyl ether (also known as methyl "Cellosolve"), propylene glycol monomethyl ether, ethylene glycol dibutyl ether (also known as dibutyl "Cellosolve"), ethylene glycol monohexyl ether (also known as n-hexyl "Cellosolve"), ethylene glycol monophenyl ether (also known as phenyl "Cellosolve"), diethylene glycol diethyl ether (also known as diethyl "Carbitol"), diethylene glycol monobutyl ether (also known as butyl "Carbitol"), diethylene glycol dibutyl ether (also known as dibutyl "Carbitol"), and diethylene glycol monohexyl ether (also known as n-hexyl "Carbitol").

In yet other embodiments, the formulations of the invention further comprise a fatty acid ester, such as propylene glycol dicaprylate/dicaprate (also known by the trade name, "miglyol"), stearyl stearate, palmitate, and myristate. Other examples of suitable neutral oils and fatty acid esters include hydrocarbonaceous vegetable oils, such as liquid triglycerides of fatty acids comprising from 4 to 24 carbon atoms (such as triglycerides, heptanoic acid and octanoic acid), sunflower oil, maize oil, soybean oil, gourd oil, grape seed oil, sesame oil, hazelnut oil, apricot oil, macadamia oil, castor oil, avocado oil, triglycerides of caprylic/capric acids (such as those commercially available as Miglyol 810, Miglyol 812 and Miglyol 818), jojoba oil and karite butter; synthetic esters, such as synthetic esters of fatty acids such as, for example, purcellin oil, isononyl isononanoate, isopropyl myristate, 2-ethylhexyl palmitate, 2-octyldodecyl stearate, 2-octyldodecyl erucate, and isostearyl isostearate.

In certain embodiments, a formulation of the invention may comprise at least two active pharmaceutical or veterinary agents.

Examples of active agents that may be used in the formulations of the invention include clorsulon, albendazole, triclabendazole, netobimin, closantel, rafoxanide, and oxyclozanide; avermectins including ivermectin, eprinomectin, a milbemycin, abamectin, doramectin, emamectin, latidectin, lepimectin, milbemectin, selamectin, and milbemycins including moxidectin and nemadectin, mixtures thereof and a salt/salts thereof. In certain embodiments, a formulation of the invention may comprise two active agents, such as a flukicide and a macrocyclic lactone. In further embodiments, the flukicide is clorsulon and the macrocyclic lactone is ivermectin or eprinomectin.

In yet other embodiments, the invention provides a method of treating or preventing a parasiticidal infection in an animal, comprising topically administering a pour-on formulation to the animal comprising a solvent system for a veterinary pour-on formulation for topical, transdermal treatment or prophylaxis of parasiticidal infection, comprising (a) an effective amount of at least one active agent; (b) a glycol ether; and (c) a stability enhancer.

The invention provides for pour-on formulations for the treatment or prophylaxis of parasites of animals, and in particular, cattle, sheep, horses, pigs, chicken, cats, and dogs, with the aim of ridding these hosts of all the parasites commonly encountered by them. In certain embodiments, the invention provides for pour-on formulations for administration to ruminants, such as cattle, comprising a combination of a flukicide and an antiparasitic macrocyclic lactone. The invention also provides for effective and lasting destruction of ectoparasites, such as fleas, ticks, mites, e.g., itch mites, mosquitoes, flies and lice, and of endoparasites, such as trematodes (e.g., liver flukes), nematodes, such as filariae, heartworms and roundworms of the digestive tract of animals and humans.

Another aim of the invention is to provide such a formulation that is quick and easy to use and entirely compatible with use on herds or flocks containing a large number of animals.

In particular this invention provides for pour-on formulations for the treatment or prophylaxis of parasite infestations in an animal, which may comprise:

(1) a solvent system for a veterinary pour-on formulation for topical, transdermal treatment or prophylaxis of parasiticidal infection, comprising
(A) an effective amount of a flukicide selected from the group consisting of clorsulon, albendazole, triclabendazole, netobimin, closantel, rafoxanide, nitroxynil, and oxyclozanide; and
(B) an effective amount of a macrocyclic lactone anthelmintic or antiparasitic agent selected from the group consisting of avermectins such as ivermectin, eprinomectin, abamectin, doramectin, emamectin, latidectin, lepimectin, and selamectin, and milbemycins such as moxidectin, nemadectin, and milbemycin oxime, mixtures thereof and a salt/salts thereof;
(2) a glycol ether; and
(3) a stability enhancer.

The invention also provides for an easy method of treating parasitic infestations or for the prophylaxis of parasite infestations in animals, which comprises topically applying to said animal an effective amount of a formulation according to the present invention.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

This invention relates to solvent systems that provide enhanced solvency and stability for one or more active pharmaceutical or veterinary agents. In certain embodiments, the inventive formulations described herein provide a high degree of solvency for an active agent, such as ivermectin or eprinomectin, by formulating the active agent in a glycol ether, such as diethylene glycol monoethyl ether or dipropylene glycol monomethyl ether. In further embodiments, the formulations of the invention additionally provide a greater degree of stability for the active agent by comprising a stability enhancer. A "stability enhancer" is a compound that enhances the stability of an active agent compared to the stability of the active agent in the absence of the stability enhancer. Examples of stability enhancers include glycerol formal and polyethylene glycol (e.g., PEG 200). In the absence of a "stability enhancer" as described herein, certain active agents can rapidly degrade and so be unavailable to have a therapeutic or prophylactic effect when administered to a target species.

In some embodiments, the solvent systems of the invention advantageously broaden the efficacy of a pharmaceutical or veterinary formulation by providing enhanced solvency for one or more active agents. For example, by providing a solvent system that enhances the solvency of an active agent, such as a parasiticidal agent, an increased amount of the active agent can be incorporated into a veterinary formulation, such as a pour-on formulation for topical, transdermal application of the agent, thereby permitting delivery of an increased amount of the agent, if desired or required, to exert its therapeutic or prophylactic effect. In addition, in yet other embodiments, a solvent system of the invention enhances the absorption and spread of the one or more active agents in a formulation, such as a pour-on formulation for topical, transdermal application of the agent to an animal.

In certain embodiments, this invention provides a pour-on formulation for the treatment and prophylaxis of parasite infestation in animals, which comprises a flukicide, an antiparasitic macrocyclic lactone, and a pharmaceutically or veterinarily acceptable liquid carrier vehicle. It has surprisingly been discovered that the stability of the subject macrocyclic lactone compounds, such as ivermectin and eprinomectin, are enhanced in glycol-ether-based pour-on formulations that comprise glycerol formal. Accordingly, in certain embodiments, formulations of the invention comprise glycerol formal.

In some embodiments, the pharmaceutically or veterinarily active agents of the subject pour-on formulations comprise a stability enhancer that is a solvent, such as glycerol formal or polyethylene glycol, which enhances the stability of the active agent, for example, the macrocyclic lactone. In certain embodiments, the formulations comprise a stability-enhancing amount of stabilized glycerol formal. In other embodiments, the formulations comprise a stability-enhancing amount of polyethylene glycol, such as PEG 200.

In some embodiments, the stability of an active agent, which is a macrocyclic lactone, of a formulation of the invention is enhanced in that less than 20% by weight of macrocyclic lactone degradation is demonstrated when the formulation is stored at 50° C. for three months. In other embodiments, less than 15% by weight of degradation is identified. In yet other embodiments, less than 10% by weight of degradation is demonstrated. In certain aspects, less than 5% by weight of macrocyclic lactone degradation is identified when a formulation comprising the macrocyclic lactone is stored at 50° C. for three months. Stability of an active agent in a formulation of the present invention can be assessed by any means known in the art. For example, stability studies of an active agent may be carried out at lower temperatures over longer periods of time to assess the stability of the active agent in a formulation of the invention. For example, storage at 50° C. for three months, as discussed above, may be done to accelerate any reaction that may occur at a lower temperature, e.g., 30° C., but that may not be manifest until over a longer period of time, e.g., six months or more.

In yet other embodiments, the invention relates to formulations that provide a high level of solvency for one or more pharmaceutical or veterinary agents. Generally, a glycol ether is employed in a formulation of the invention in order to achieve good solvency of the antiparasitic agent to be dissolved in the formulation. In addition, the formulations of the invention will typically enhance the absorption and spread of the pharmaceutical or veterinary agents dissolved therein.

Examples of glycol ethers that can be employed in the formulations of the invention include diethylene glycol monoethyl ether, dipropylene glycol monomethyl ether, propylene glycol monomethyl ether, tripropylene glycol monomethyl ether, ethylene glycol monoethyl ether, and ethylene glycol monomethyl ether.

In certain embodiments, a fatty acid ester, such as propylene glycol dicaprylate/dicaprate, is employed in addition to a glycol ether to enhance the solvency of the active agent.

In particular embodiments, a small amount of glycerol formal, e.g., 5% or less, is added in the inventive formulations described herein, which enhances the stability of the pharmaceutical or veterinary agent or agents dissolved therein. In some embodiments, it may be desirable to add PEG 200 to the formulations of the invention to support the stability enhancement and solvency function of the glycerol formal. Glycerol formal is the mixture of 5-hydroxy-1,3-dioxane and 4-hydroxymethyl-1,3-dioxolane (60:40). In preferred embodiments, the glycerol formal that is added to a formulation of the invention is stabilized glycerol formal. Stabilized glycerol formal typically contains 0.02% disodium EDTA, 0.02% N-propyl gallate, and 0.01% thiopropionic acid. Glycerol formal, as defined herein, includes stabilized glycerol formal.

In other embodiments, the stability enhancer is a polyethylene glycol (PEG). In some embodiments, a high molecular weight PEG is employed in the formulation. In other embodiments, a low molecular weight PEG is employed in the formulation. Additional examples of suitable polyethylene glycols include tetraglycol and propylene glycol.

The invention further provides for titration of the amount of stability enhancer that is added to the formulations of the invention. For example, in embodiments where the stability enhancer is glycerol formal, the amount of glycerol formal can be titrated, such that an optimal stability of a pharmaceutical or veterinary agent is achieved in the formulation.

In certain embodiments, the formulations of the invention provide for enhanced solvency of ecto- and endoparasiticidal agents, such as macrocyclic lactones and flukicides, respectively. For example, in certain embodiments, the invention provides a formulation comprising about 17.5% w/v clorsulon and about 0.5% w/v ivermectin. In other embodiments, the invention provides a formulation comprising about 17.5% w/v clorsulon and about 0.1% w/v ivermectin. In some embodiments, the invention provides a formulation comprising about 10% w/v clorsulon and about 0.5% w/v eprinomectin. In other embodiments, the inventive formulation comprises about 10% w/v clorsulon and about 1.0% w/v eprinomectin. In yet other embodiments, the invention provides formulations comprising less than 17.5% w/v clorsulon in combination with a macrocyclic lactone, such as 10% w/v or less of the macrocyclic lactone. In other embodiments, the invention provides a formulation comprising greater than 17.5% w/v clorsulon in combination with a macrocyclic lactone, such as 10% w/v or less of the macrocyclic lactone. In particular embodiments, the amount of clorsulon present in a formulation of the invention is at least about 4% w/v to about 17.5% w/v. In certain embodiments, the amount of macrolide in a formulation of the invention is about 0.25% w/v. In other embodiments, the amount of macrolide is about 0.75% w/v.

The amount of the one or more antiparasiticidal agents in a formulation of the invention may be adjusted to achieve the desired bioavailability of the agent in the animal to which the formulation is to be administered. For example, in certain embodiments, a formulation of the invention comprises about 0.5% w/v of a macrocyclic lactone. It may be desirable to increase the bioavailability of the macrocyclic lactone in this embodiment by doubling the amount of the macrocyclic lactone in the formulation to about 1.0% w/v. In other embodiments, it may be desirable to increase the amount of macrolide in a formulation from about 0.5% w/v to about 0.75% w/v.

Dosing volume of a formulation of the invention can also be adjusted as desired. Typically, the dose volume of a formulation of the invention will be about 1 mL/10 kg. In certain embodiments, the dose volume of a formulation of the invention is about 1 mL/20 kg.

In certain embodiments, the invention provides a solvent system for a veterinary pour-on formulation for topical, transdermal treatment or prophylaxis of parasiticidal infection, comprising:
(a) an effective amount of at least one active agent;
(b) a glycol ether; and
(c) a stability enhancer.

In some embodiments, the invention provides pour-on compositions, wherein the composition comprises:
(A) a pharmaceutically or veterinarily effective amount of a flukicide; and
(B) a pharmaceutically or veterinarily effective amount of a macrocyclic lactone anthelmintic or antiparasitic agent;
(C) a glycol ether; and
(D) a stability enhancer.

In further embodiments, the invention provides a pour-on formulation for the treatment and prophylaxis of parasite infestation in cattle, which comprises
(1) a composition comprising
(A) a pharmaceutically or veterinarily effective amount of a flukicide selected from the group consisting of clorsulon, albendazole, triclabendazole, netobimin, closantel, rafoxanide, nitroxynil and oxyclozanide; and
(B) a pharmaceutically or veterinarily effective amount of a macrocyclic lactone anthelmintic or antiparasitic agent selected from the group consisting of avermectins such as ivermectin, eprinomectin, abamectin, doramectin, emamectin, latidectin, lepimectin, and selamectin, and milbemycins such as moxidectin, nemadectin, and milbemycin oxime, mixtures thereof and a salt/salts thereof;
(2) a glycol ether; and
(3) a stability enhancer.

In some embodiments, this invention provides for a pour-on formulation which comprises:
(1) a composition comprising
(A) an effective amount of at least one compound of the formula

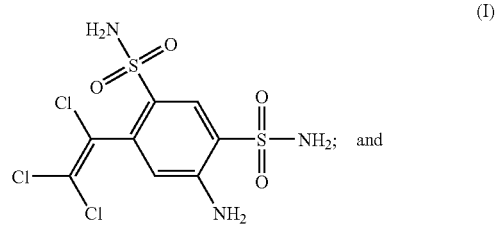

(B) an effective amount of a macrocyclic lactone selected from the group consisting of avermectins, ivermectin, abamectin, doramectin, emamectin, eprinomectin, latidectin, lepimectin, milbemectin, moxidectin, selamectin, milbemycins and their derivatives with ivermectin and eprinomectin being especially preferred;
(2) a glycol ether selected from the group consisting of diethylene glycol monoethyl ether, dipropylene glycol monomethyl ether, propylene glycol monomethyl ether, tripropylene glycol monomethyl ether, ethylene glycol monoethyl ether, ethylene glycol monomethyl ether, a mixture of at least two of these solvents, a mixture of at least three of these solvents, and a mixture of at least four of these solvents; and
(3) a stability enhancer selected from the group consisting of glycerol formal and polyethylene glycol.

In certain embodiments, both compounds of formula I and a macrocyclic lactone anthelmintic or antiparasitic agent such as ivermectin or eprinomectin are present in a glycol ether-based formulation comprising glycerol formal.

In certain embodiments, the invention provides pour-on compositions, wherein the composition comprises:
(A) clorsulon;
(B) ivermectin;
(C) a glycol ether; and
(D) glycerol formal; or
wherein the composition comprises
(A) clorsulon;
(B) eprinomectin;
(C) a glyol ether; and
(D) glycerol formal.

The expression "pour-on formulation" or "pour-on skin solution" is understood to refer to a ready-to-use solution intended to be applied topically and locally on the animal, preferably on the animal's back and at several points or along the line of the back, and applied in low volume, advantageously about 5 to 20 ml per 100 kg, advantageously about 10 ml per 100 kg, with a total volume of from 10 to 150 ml per animal, advantageously 50 ml. Pour-on formulations are described in U.S. Pat. No. 6,010,710, incorporated herein by reference.

In some embodiments, it is expected that upon application, the active ingredients of the subject formulations will cross the cutaneous barrier and be taken up into the bloodstream.

This thereby affords both a perfect compatibility with the restrictions of use in extensive grazing, in terms of ease of use in particular, and a spectrum of activity and of efficacy, as well as a period of efficacy, which are suited to this type of rearing.

In some embodiments, the invention provides for pour-on formulations comprising a flukicide that is effective in the treatment or prevention in an animal of adult flukes and later stages of immature migrating flukes. In other embodiments, the flukicide is effective primarily against adult liver flukes. In yet other embodiments, the flukicide is effective in the treatment or prevention of adult liver flukes only.

An example of a flukicide suitable for use in the formulations of the invention is clorsulon, which is a compound also known as MK-401 (a Merck compound). See, for example, U.S. Pat. Nos. 4,001,406 and 4,062,952, incorporated herein by reference. Accordingly, in some embodiments, the invention provides pour-on formulations comprising a compound of the formula

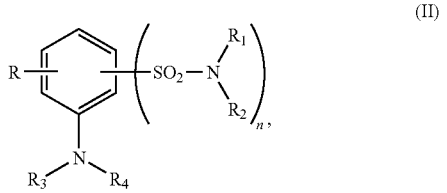

(II)

wherein
R is $C_1$-$C_8$ alkyl, $C_1$-$C_8$ haloalkyl, $C_2$-$C_8$ alkenyl, $C_2$-$C_8$ haloalkenyl, cycloalkyl or phenyl, $R_1$ and $R_2$ are independently H, $C_1$-$C_8$ alkyl,
$R_3$ and $R_4$ are independently H, $C_1$-$C_8$ alkyl, and
n is 2.

In certain embodiments, the invention provides pour-on formulations comprising a compound of formula (I).

Macrocyclic lactone anthelmintic or antiparasitic agents ("compounds B") are well known to a person skilled in the art and are easily obtained either commercially or through techniques know in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may in particular be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 677,054. For latidectin, "International Nonproprietary Names for Pharmaceutical Substances (INN)". World Health Organization (WHO) Drug Information, vol. 17, no. 4, page 278-279, (2003), may in particular be consulted.

Compounds (B) are either natural products or are semi-synthetic derivatives thereof. The structure of at least certain compounds (B) are closely related, e.g., by sharing a complex 16-membered macrocyclic lactone ring. The natural product avermectins are disclosed in U.S. Pat. No. 4,310,519 to Albers-Schönberg, et al., and the 22,23-dihydro avermectin compounds are disclosed in Chabala, et al., U.S. Pat. No. 4,199,569. Mention is also made of Kitano, U.S. Pat. No. 4,468,390, Beuvry et al., U.S. Pat. No. 5,824,653, European Patent Application 0 007 812 A1, published Jun. 2, 1980, U.K. Patent Specification 1 390 336, published Apr. 9, 1975, European Patent Application 0 002 916 A2, and Ancare New Zealand Patent No. 237 086, inter alia. Naturally occurring milbemycins are described in Aoki et al., U.S. Pat. No. 3,950,360 as well as in the various references cited in "The Merck Index" 12th ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920,148 and EP 667,054.

Particularly preferred macrocyclic lactones are avermectin derivatives which are monosaccharides and have a 5-oxime substituent. Particularly preferred derivatives are:

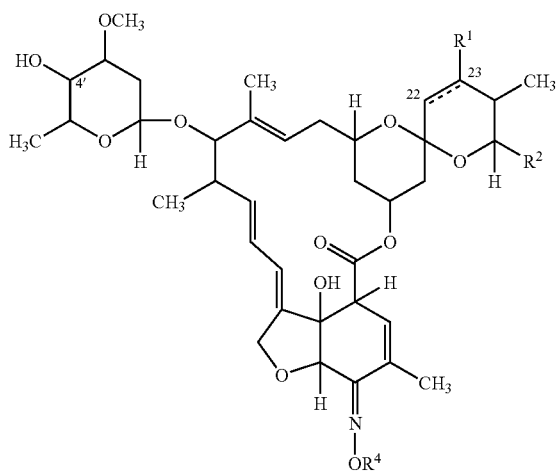

wherein the broken line at the 22-23 position represents an optional bond, R1, when present, is a hydrogen or a hydroxyl group, R2 is, for example, alkyl or cycloalkyl group and R3 is, for example, hydrogen or alkyl. An especially preferred compound of this general structure is selamectin which has the following structure:

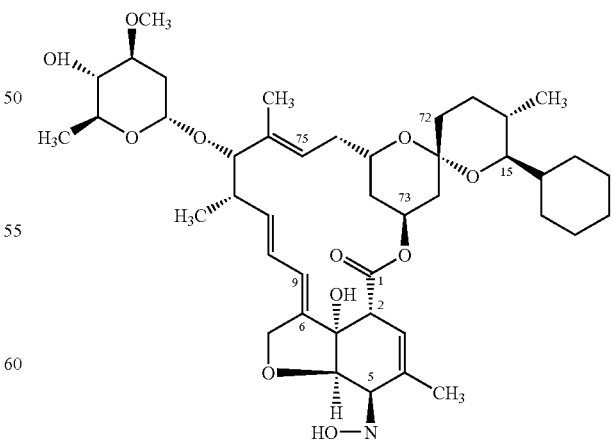

These compounds are known in the art and are described for example in EP 667,054. An other especially preferred compound is emamectin, which has the following structure:

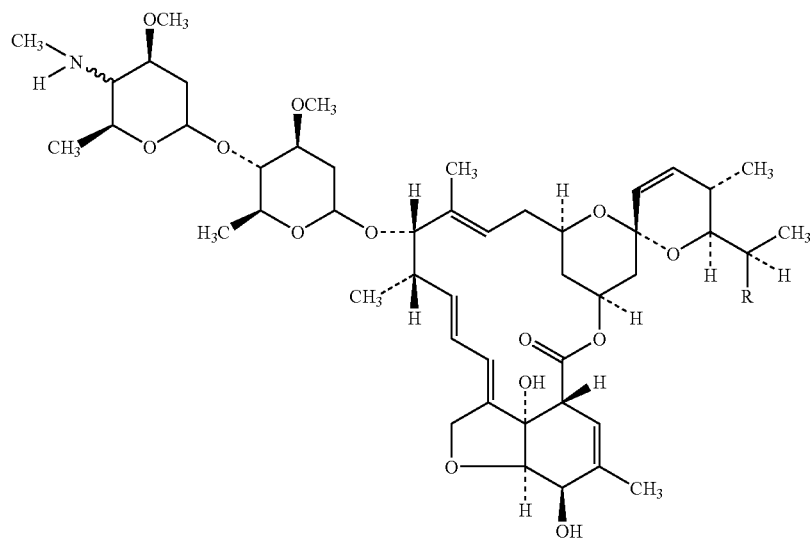

where R is —CH$_2$CH$_3$ or —CH$_3$,
or a salt of this compound. These compounds are described in U.S. Pat. No. 4,874,749 or 5,288,710.

Other preferred macrocyclic lactones are avermectin derivatives where the C-13 position of the lactone ring is substituted with an ester-based moiety such as latidectin:

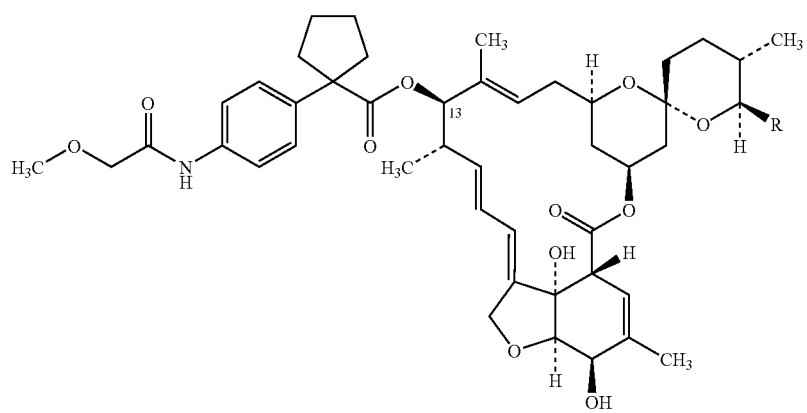

component A3=R=CH2CH3
component A4=R=CH3; or
lepimectin:

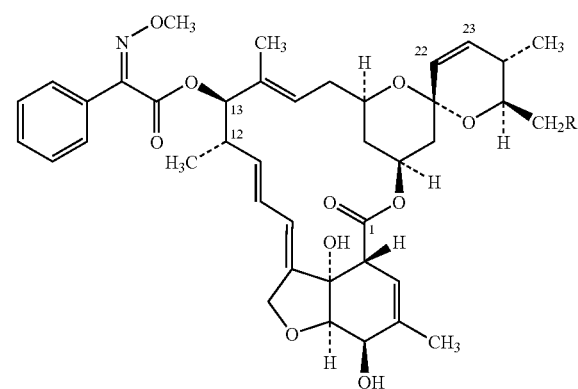

R=CH2CH3 (major component)
R=CH3 (minor component).

These ester based derivatives can also be viewed as intermediate compounds which can be converted to milbemycin-type compounds by cleaving the ester moiety at the C-13 position and further converted to avermectin-type compounds by glycosylating the subsequently free —OH at the C-13 position. These conversions can be accomplished via synthetic organic techniques well-known in the art, see e.g. "Protecting Groups in Organic Synthesis (Third Edition)", by Green & Wuts, Wiley-Interscience, (1999); "Preparative Carbohydrate Chemistry", edited by Stephen Hanessian, Marcel-Dekker, Inc., (1997); "Monosaccharides—Their Chemistry and Their Roles in Natural Products", Collins & Ferrier, John Wiley & Sons, (1995).

For example, cleaving the ester moieties of latidectin and lepimectin and glycosylating with a 2,6-dideoxy-3-O-methyl-4-O-(2,4,6-trideoxy-3-O-methyl-4-methylamino-α-L-lyxo-hexapyranosyl)-α-L-arabino-hexapyranoside results in a homolog and an isomer of emamectin respectively.

Also contemplated are the pharmaceutically or veterinarily acceptable acid or base salts, where applicable, of the active compounds provided for herein. The term "acid" contemplates all pharmaceutically or veterinarily acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinarily acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

Preferred salts for emamectin include the acid mineral salts, such as the hydrochloride, nitrate, sulfate, phosphate salts, and the organic acids such as the tartarate and malate salts. Especially preferred salts are salts of the formula:

c) benzenesulfonic acid,
d) citric acid,
e) phosphoric acid,
f) tartaric acid, or
g) maleic acid.

For the chemical preparation of the products of the invention, a person skilled in the art is regarded as having at his or her disposal, inter alia, the entire contents of "Chemical Abstracts" and of the documents that are cited therein.

Administration of the inventive formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation.

Pour-on formulations of the invention typically comprise a glycol ether and stability enhancer and may be prepared by dissolving the active ingredient(s) into the glycol ether. In other embodiments, in addition to a glycol ether, another pharmaceutically or veterinarily acceptable vehicle may be used. These formulations will vary with regard to the weight of the therapeutic agent in the combination depending on the species of host animal to be treated, the severity and type of infection and the body weight of the host. The compounds may be administered continuously, particularly for prophylaxis, by known methods. It is well within the routine skill of the practitioner to determine a particular dosing regimen for a specific host and parasite.

The invention also relates to such a method with a therapeutic aim intended for the treatment and prevention of parasitoses having pathogenic consequences.

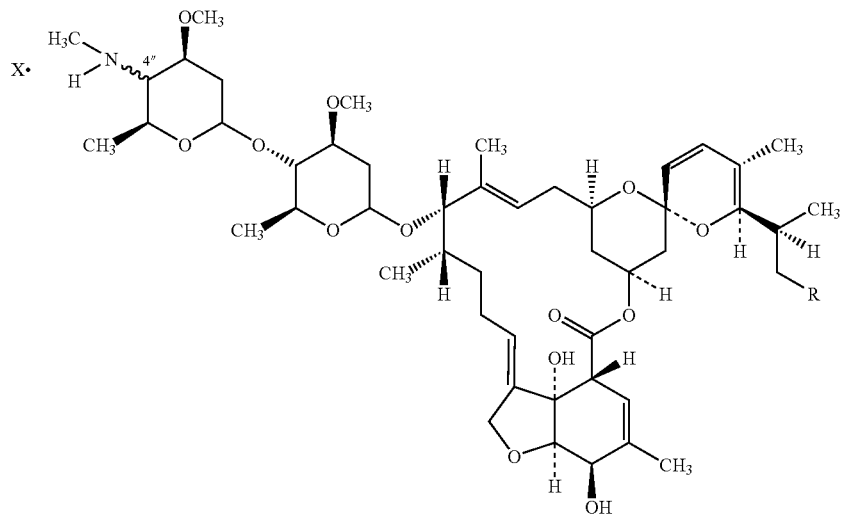

wherein
R is hydrogen or methyl; and
X is:
a) benzoic acid,
b) benzoic acid substituted with one, two, or three substituents selected from the group consisting of:
halogen (Cl, Br, F, I),
hydroxyl,
carboxyl,
(C1-C6)-alkyl, and
(C1-C6)-alkoxyl, The glycol ether in the inventive formulations will advantageously be present in an amount effective to enhance the solvency of the one or more active agents. For example, in some embodiments, a formulation of the invention will comprise a glycol ether in an amount of about 30-85% w/v, such as about 50-75% w/v or about 60-75% w/v. In other embodiments, the amount of glycol ether will be about 30-45% w/v, about 40-55% w/v, about 50-65% w/v, about 55-70% w/v, about 70-85% w/v. In yet other embodiments, the amount of glycol ether will be about 55% w/v, about 60% w/v, about 65% w/v, about 70% w/v, about 75% w/v. The amount of glycol ether will generally be optimized to enhance the dissolution of the desired amount of active agent in the formulation. For example, in some embodiments, the active agent is ivermectin in an amount of about 0.5% w/v, and the amount of glycol ether in the formulation is about 70% w/v. In other embodiments, the active agent is ivermectin in an amount of about 0.5% w/v, and the amount of glycol ether in the formulation is about 65% w/v.

In yet other embodiments, the formulation comprises two active agents, for example, ivermectin in an amount of about 0.5% w/v and clorsulon in an amount of about 17.5% w/v, and the glycol ether is present in an amount of about 65-70% w/v. In certain embodiments, a formulation of the invention comprises a macrolide, such as ivermectin or eprinomectin, in an amount of about 0.5% w/v to about 1.5% w/v and a flukicide, such as clorsulon, in an amount of about 4% w/v to about 20% w/v, and the glycol ether is present in an amount of about 35-85% w/v, of about 40-45% w/v, of about 55-60% w/v, or about 65-70% w/v.

In other embodiments, it will be advantageous to increase or decrease the amount of glycol ether to enhance the solvency of the active agent to be dissolved therein. For example, a formulation comprising 65% w/v of a glycol ether, such as dipropylene glycol monomethyl ether, may be modified to comprise a greater amount of the glycol ether, such as, e.g., 70% w/v, to enhance the solvency of the active agent being dissolved therein.

In yet other embodiments, a formulation of the invention comprises more than one glycol ether.

In further embodiments, a fatty acid ester, such as propylene glycol dicaprylate/dicaprate, is added to the formulation to increase the solvency of the active agent.

In general, solvents will be used in proportion with the concentration of the subject compounds and their solubility in the solvent.

In addition to enhancing the solvency of an active agent, the solvent systems of the invention may comprise stability enhancers, which enhance the stability of the active agent in the formulation. Examples of stability enhancers include glycerol formal and polyethylene glycol (e.g., PEG 200). The amount of stability enhancer present in a formulation of the invention may be low, such as about 5% w/v or less (e.g., 1.5% w/v). In other embodiments, the stability enhancer will be present in an amount of about 5-25% w/v, such as, for example, 15% w/v. In still other embodiments, enhanced stability of the active agent may be reached with addition of a stability enhancer in an amount that is greater than 25% w/v. The solutions according to the invention, which are advantageously oily, in addition to a glycol ether, may comprise a diluent or vehicle and also a solvent (organic solvent) for the active agent(s).

Organic solvents which can be used in the invention include acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents.

In addition, mention may be made in particular of:
plant oils such as soybean oil, groundnut oil, castor oil, corn oil, cotton oil, olive oil, grape seed oil, sunflower oil, etc.; mineral oils such as petrolatum, paraffin, silicone, etc.; aliphatic or cyclic hydrocarbons or alternatively, for example, medium-chain (C8 to C12 in particular) triglycerides.

An emollient and/or spreading and/or film-forming agent may additionally be added, this agent being selected in particular from:
polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils, in particular polydimethylsiloxane (PDMS) oils, for example those containing silanol functionalities, or a 45V2 oil,
anionic surfactants such as alkaline stearates, in particular sodium, potassium or ammonium stearates; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil,
cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, amine salts of formula $N^+R'R''R'''$ in which the radicals R are optionally hydroxylated hydrocarbon radicals; octadecylamine hydrochloride is among the cationic surfactants which can be used, nonionic surfactants such as sorbitan esters, which are optionally polyoxyethylenated, in particular polysorbate 80, polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as the substituted lauryl compounds of betaine; or a mixture of at least two of these agents.

The emollient may be used in a proportion of from 0.1 to 10%, in particular from 0.25 to 5%, by volume.

The subject of the present invention is also a process for the elimination of parasites, such as liver flukes, from cattle and sheep using a direct pour-on skin solution according to the present invention, so as to obtain long-lasting and broad-spectrum efficacy, the solution being applied to the animal's back, preferably along the line of the back at one or more points.

According to a first embodiment, the process consists in applying the solution to the animals in pasture and/or before they arrive in pasture, the application preferably being repeated every month, preferably every two months.

According to a second embodiment, the process consists in applying the solution to the animals before they arrive in the "feed lot", it being possible for this application to be the final one before the animals are slaughtered.

The process may also consist in combining these two embodiments, namely the first followed by the second.

In all cases, the efficacy advantageously makes it possible to stop any application 1 to 3 months before slaughter, in particular between 1.5 and 2.5 months, more particularly about two months before slaughter.

The solutions according to the invention may be applied using any means known per se, such as using an applicator gun or a metering flask.

In some embodiments, the organic solvent for the liquid carrier vehicle will have a dielectric constant of between about 10 and about 35, preferably between about 20 and about 30, the content of this solvent in the overall composition preferably representing the remainder to 100% of the composition. It is well within the skill level of the practitioner to select a suitable solvent on the basis of these parameters.

In some embodiments, the organic cosolvent for the liquid carrier vehicle will have a boiling point of less than about 100° C., preferably of less than about 80° C., and will have a dielectric constant of between about 10 and about 40, preferably between about 20 and about 30; this cosolvent can advantageously be present in the composition according to a weight/weight (w/w) ratio with respect to the solvent of between about 1/15 and about 1/2; the cosolvent is volatile in order to act in particular as drying promoter and is miscible with water and/or with the solvent. Again, it is well within the skill level of the practitioner to select a suitable solvent on the basis of these parameters.

The organic solvent for the liquid carrier includes the commonly acceptable organic solvents known in the formulation art. These solvents may be found, for example, in Remington Pharmaceutical Science, 16th Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as C8-C10 caprylic/capric triglyceride (Estasan or Miglyol 812), oleic acid or propylene glycol.

The liquid carrier may also comprise a microemulsion. Microemulsions are also well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase preferably comprises triglycerides and more preferably medium-chain triglycerides, for example C8-C10 caprylic/capric triglyceride. The oily phase will represent, in particular, from about 2 to about 15%, more particularly from about 7 to about 10%, preferably from about 8 to about 9%, v/v of the microemulsion.

The aqueous phase includes, for example water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolysed C8-C10 glycerides or polyglyceryl-6 dioleate. In addition to these surfactants, the cosurfactants include short-chain alcohols, such as ethanol and propanol.

Some compounds are common to the three components discussed above, e.g., aqueous phase, surfactant and cosurfactant. However, it is well within the skill level of the practitioner to use different compounds for each component of the same formulation.

The cosurfactant to surfactant ratio will preferably be from about 1/7 to about 1/2. There will preferably be from about 25 to about 75% v/v of surfactant and from about 10 to about 55% v/v of cosurfactant in the microemulsion.

Likewise, the co-solvents are also well known to a practitioner in the formulation art. Preferred co-solvents are those that promote drying and include, for example, absolute ethanol, isopropanol (2-propanol) or methanol.

The formulation can also comprise an antioxidizing agent intended to inhibit oxidation in air, this agent being in particular present in a proportion of about 0.005 to about 1% (w/v), preferably of about 0.01 to about 0.05%.

Crystallization inhibitors which can be used in the invention include:

polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, or preferably a mixture of at least two of the compounds listed above.

In a particularly preferred embodiment, a crystallization inhibitor pair will be used. Such pairs include, for example, the combination of a film-forming agent of polymeric type and of a surface-active agent. These agents will be selected in particular from the compounds mentioned above as crystallization inhibitor.

Particularly preferred film-forming agents of polymeric type include:
  the various grades of polyvinylpyrrolidone,
  polyvinyl alcohols, and
  copolymers of vinyl acetate and of vinylpyrrolidone.

Especially preferred surface-active agents, include those made of non-ionic surfactants, preferably polyoxyethylenated esters of sorbitan and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

This invention also provides for the use of at least one compound of formula (I) and of at least one compound of type (B), as defined above, in the preparation of a composition as defined above.

Other advantages and characteristics of the invention will become apparent on reading the following description, given by way of non-limiting examples.

EXAMPLES

Example 1

Formulation

Experiments were conducted to establish the effective solubility of clorsulon and ivermectin when combined at certain concentrations. In solubility experiments, actives were trialed at double the target concentration in order to assess the solubility potential with the possible addition of supplementary diluting excipients.

The initial solubility screen demonstrated a range of solvents with the ability to solubilize the active ingredients at approximately 200% nominal concentration (summarized in Table 1). In addition to examination of solutions for clarity, aged samples (2 months@ 25° C.) were examined chromatographically for degradation. Through forced degradation studies it was shown that clorsulon is the more stable of the two active compounds, and therefore ivermectin was used as the initial marker to indicate product stability. These data provided an indication of excipient compatibility.

TABLE 1

| SAMPLE ID | SOLVENT/MIXTURE | EVALUATION |
|---|---|---|
| 01 | Glyceryl Formal (GF) | Soluble with 10 mins sonication |
| 02 | Propylene Glycol (PG) | Soluble with 15 mins sonication |
| 04 | N-methyl Pyrrolidone | Soluble with 10 mins sonication |
| 06 | Propylene Carbonate | Soluble with 10 mins sonication |
| 08 | Arcosolv DPM (ACS) | Soluble with 10 mins sonication |
| 10 | Tetraglycol | Soluble with 15 mins sonication |
| 11 | Carbitol (Transcutol) (CBT) | Soluble with 10 mins sonication |
| 12 | GF/PG 50:50 | Soluble with 10 mins sonication |
| 15 | PEG 200/CBT 60:40 | Not soluble after sonication but dissolves over time |

The data in Table 2 relate to chromatographic area % of the ivermectin B1b component.

TABLE 2

Area % Ivermectin B1a

| SAMPLE ID | SOLVENT/MIXTURE | AREA % IVERMECTIN |
|---|---|---|
| 01 | Glyceryl Formal (GF) | 96.1 |
| 02 | Propylene Glycol (PG) | 80.8 |
| 04 | N-methyl Pyrrolidone | 70.8 |
| 06 | Propylene Carbonate | Nil |
| 08 | Arcosolv DPM (ACS) | 77.7 |
| 10 | Tetraglycol | 86.1 |
| 11 | Carbitol (Transcutol) (CBT) | 71.4 |
| 12 | GF/PG 50:50 | 95.6 |
| 15 | PEG 200/CBT 60:40 | 92.6 |

The novel stabilizing effect of glycerol formal was incorporated into subsequent formulations along with the use of the ingredient, miglyol 840 (propylene glycol dicaprylate/dicaprate).

A series of small volume (5-10 mL) samples were prepared incorporating miglyol 840 and glycerol formal. Details of these formulations are shown in Table 6.

Samples were prepared by addition of the active ingredient(s) to a 20 mL, screw-capped glass vial. Solvents/excipients were added and the vial shaken/sonicated at room temperature to dissolve the active pharmaceutical ingredient(s) (API(s)) and the sample homogenized by shaking.

Larger batches (100 mL) of formulations were made for use in preliminary stability studies.

Eprinomectin was also included in the formulation studies at the same end product concentration as ivermectin (0.5% w/v). The formulations shown in Table 3 were monitored for stability.

Table 4 shows details of the stability data generated from the Table 3 formulations.

TABLE 3

Stability Formulation Summary

| | Formulation Details | | | | | | | | | | |
|---|---|---|---|---|---|---|---|---|---|---|---|
| Formulation | IVN | EPN | CLS | Carbitol | Arcosolv | PEG 200 | GF | Miglyol 840 | IPA | CAP | TEA |
| 1 | 0.5 | — | 17.5 | 70 | — | — | 5 | 25 | — | — | — |
| 2 | 0.5 | — | 17.5 | — | 65 | — | 5 | 30 | — | — | — |
| 3 | 0.5 | — | 17.5 | — | — | — | 15 | — | 65 | 15 | 0.05 |
| 4 | 0.5 | — | 17.5 | — | 65 | — | 5 | 30 | — | — | — |
| 5 | 0.5 | — | 17.5 | — | 70 | 5 | — | 25 | — | — | — |
| 6 | 0.5 | — | 17.5 | 75 | — | — | — | 25 | — | — | — |
| 7 | 0.5 | — | 17.5 | 75 | — | — | — | 25 | — | — | — |
| 8 | — | 0.5 | 17.5 | 70 | — | — | 5 | 25 | — | — | — |
| 9 | — | 0.5 | 17.5 | — | 65 | — | 5 | 30 | — | — | — |

Carbitol = Transcutol

TABLE 4

| | CLS mg/g | | | | | IVN/EPN mg/g | | | |
|---|---|---|---|---|---|---|---|---|---|
| Formulation Number | Initial | 1M 50° C. | 2M 50° C. | 3M 50° C. | % Change | Initial | 1M 50° C. | 2M 50° C. | 3M 50° C. | % Change |
| 1 | 144 | 148 | 140 | 146 | 1.5 | 4.03 | 3.89 | 3.81 | 3.79 | −6.0 |
| 2 | 149 | 153 | 146 | 154 | 3.4 | 4.08 | 4.05 | 3.95 | 3.94 | −3.4 |
| 3 | 176 | 175 | 181 | 175 | −0.6 | 4.71 | 4.69 | 4.76 | 4.63 | −1.7 |
| 4 | 151 | 151 | 154 | 155 | 2.8 | 4.01 | 4.00 | 4.03 | 4.01 | 0.0 |
| 5 | 148 | 151 | 144 | 150 | 1.6 | 4.09 | 3.76 | 3.75 | 3.78 | −7.6 |
| 6 | 146 | 146 | 142 | 147 | 1.1 | 4.07 | 2.85 | 2.76 | 2.89 | −29.0 |
| 7 | 145 | 146 | 142 | 149 | 3.1 | 4.04 | 2.03 | 1.90 | 2.03 | −49.8 |
| 8 | 151 | 145 | 148 | 147 | −2.6 | 4.29 | 4.10 | 4.18 | 3.86 | −10.0 |
| 9 | 153 | 150 | 153 | 156 | 1.6 | 3.90 | 4.26 | 4.32 | 4.30 | 10.3 |

Stability Overview

Analysis of these data indicated that clorsulon is essentially stable in all formulations. In common with ivermectin batches, eprinomectin is stabilized by the addition of glycerol formal. In addition, the discovery that PEG afforded some stabilization to the formulation is equally novel.

Formulations 1, 2 and 3 of Table 3 can be prepared in suitable quantity to supply product for an in-vivo pharmacokinetic (PK) and efficacy study. Concomitant with this study, samples of these formulations were placed on stability at 30° C., 40° C. and 50° C. (ambient RH) in HDPE (high density polyethylene) bottles. Batches of product (1 L) were prepared in accordance with Table 7 and were tested using the developed analytical methods described below. Analytical data for these batches are shown in FIG. 1.

The stability test data pertaining to these batches, detailed in Table 5, indicates that over the three-month storage period batches remained stable at all storage conditions.

Table 6 depicts various formulations of active agent in glycol ethers, glycerol formal and Miglyol 840 (% v/v) (propylene glycol dicaprylate/dicaprate).

Table 7 depicts various clorsulon and ivermectin combination formulations, which were prepared and employed in in vivo pharmacokinetic studies in cattle. These pharmacokinetic study results are presented in FIGS. 2-5.

Eprinomectin and clorsulon combination formulations were also prepared and employed in in vivo pharmacokinetic studies in cattle. These formulations are presented in Table 8. Stability studies pertaining to the Table 8 formulations are detailed in Table 9. The in vivo pharmacokinetic study results pertaining to eprinomectin are presented in FIGS. 6-7.

In addition, eprinomectin and clorsulon combination formulations were also similarly prepared containing concentrations of clorsulon that were less than 10% w/v, namely, eprinomectin and clorsulon combination formulations wherein the concentration of clorsulon was either 7.5% w/v or 5% w/v.

Example 2

Analytical Methodology

In order to evaluate the stability of formulations, analytical methods (described below) were developed to assay each active ingredient and monitor any degradation.

Ivermectin Assay & Degradation Identification

This HPLC assay was developed as an external standardization method which involves volumetric dilution of an accurately weighed amount of standard material and sample. The chromatographic method comprises an isocratic elution and detection of analyte components using the run parameters below:

TABLE 10

| CONDITION | SETTING |
|---|---|
| Column: | Onyx monolithic C18, 100 × 4.5 mm |
| Column Temperature: | 30° C. |
| Mobile Phase: | 100% (acetonitrile: water 70:30) |
| Flow Rate: | 1.0 mL/min |
| Wavelength: | 246 nm |
| Injection Volume: | 20 1.1 L |
| Run Time: | 25 min |

Clorsulon Assay & Degradation Identification

This HPLC assay was developed as an external standardization method which involves volumetric dilution of an accurately weighed amount of standard material and sample. The chromatographic method comprises an isocratic elution and detection of analyte components using the run parameters below:

TABLE 11

| CONDITION | SETTING |
|---|---|
| Column: | Onyx monolithic C18, 100 × 4.5 mm |
| Column Temperature: | 25° C. |
| Mobile Phase: | 100% (acetonitrile: water 21:79) |
| Flow Rate: | 2.0 mL/min |
| Wavelength: | 268 nm |
| Injection Volume: | 2 µL |
| Run Time: | 20 min |

In order to elucidate possible degradation components, solutions of active components were subjected to forced degradation conditions of acid, base, and peroxide at elevated temperature.

Samples containing ivermectin and clorsulon were prepared in acetonitrile and subjected to acid (a few drops of phosphoric acid), alkaline (a few drops of 1N sodium hydroxide) and peroxide (a small amount of t-butyl peroxide or hydrogen peroxide) degradation conditions. Samples were first analyzed for signs of degradation after a few days at ambient temperature. If, after this time there were no signs of degradation the samples were further 'stressed' by storage at 40° C.

Example 3

Pharmacokinetic Data

HPLC assay methods are provided below that were used for determination of ivermectin and clorsulon levels, respectively, in plasma from cattle to which the indicated ivermectin and clorsulon combination formulations (FIGS. 2-5) had been topically applied. For ivermectin, an internal standardization method using Avermectin B1 was used involving extraction with ethyl acetate and derivatization by sequential addition of triethylamine and trifluoroacetic anhydride. The chromatographic method comprised an isocratic elution and detection of analyte components using the run parameters shown below.

HPLC Operating Conditions for Ivermectin $B_{1a}$ Analysis:

TABLE 12

Analysis of ivermectin $B_{1a}$ and avermectin $B_{1a}$

| | |
|---|---|
| Elution mode | Isocratic |
| Mobile phase | Acetonitrile: Tetrahydrofuran: MilliQ Water (56:30:14) |
| Flow rate | 1.6 mL/min |
| Sample injection volume | 5-10 µL |
| Detection wavelength (fluorescence) | 470 nm |
| Excitation wavelength (fluorescence) | 360 min |
| Run time | Approx 10 min |
| Elution time (avermectin $B_{1a}$ IS) | 3.95-4.74 min |
| Elution time (ivermectin $B_{1a}$) | 5.77-7.18 min |

For clorsulon, an internal standardization method using phenacetin was used involving extraction with acetonitrile. The chromatographic method comprised an isocratic elution and detection of the analyte components using the run parameters shown below.

HPLC Operating Conditions for Clorsulon Analysis:

TABLE 13

Analysis of clorsulon and phenacetin

| | |
|---|---|
| Elution mode | Isocratic |
| Mobile phase | Acetonitrile: 0.1M Potassium phosphate dibasic buffer pH 7 in Milli-Q water (3:7) |
| Flow rate | 1.0 mL/min |
| Sample injection volume | 5-10 µL |
| Detection wavelength (λ absorbance) | 265 nm |
| Run time | 10 min |
| Elution time (phenacetin internal standard) | 4.29-5.18 min |
| Elution time (clorsulon) | 5.91-7.69 min |

Figure 3:
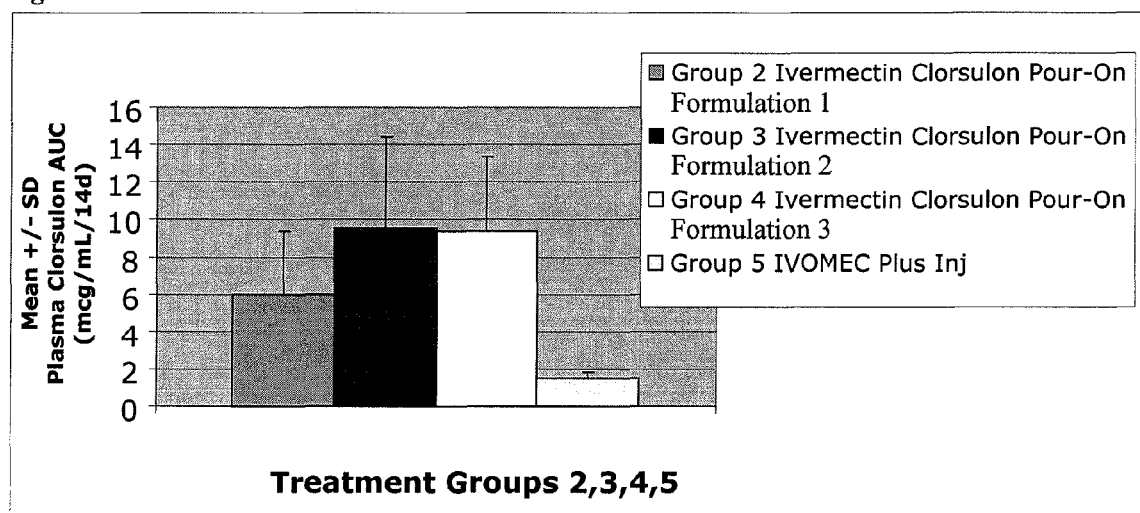
FIG. 3 is a bar graph depicting mean plasma clorsulon levels in various treatment groups.

Pharmacokinetic data pertaining to clorsulon are presented in FIGS. 2-3. From these results, each of the pour-on formulations (17.5% w/v clorsulon) appear to be significantly more bioavailable than clorsulon in the commercial injectable formulation of IVOMEC Plus (2% w/v clorsulon). These findings suggest that clorsulon is adequately absorbed from these formulations following topical application and that flukicide activity should be readily achievable. In addition, in some embodiments, the clorsulon concentration can be lowered to 10% or 5% w/v, with significant benefits for potential value equation.

Figure 4:
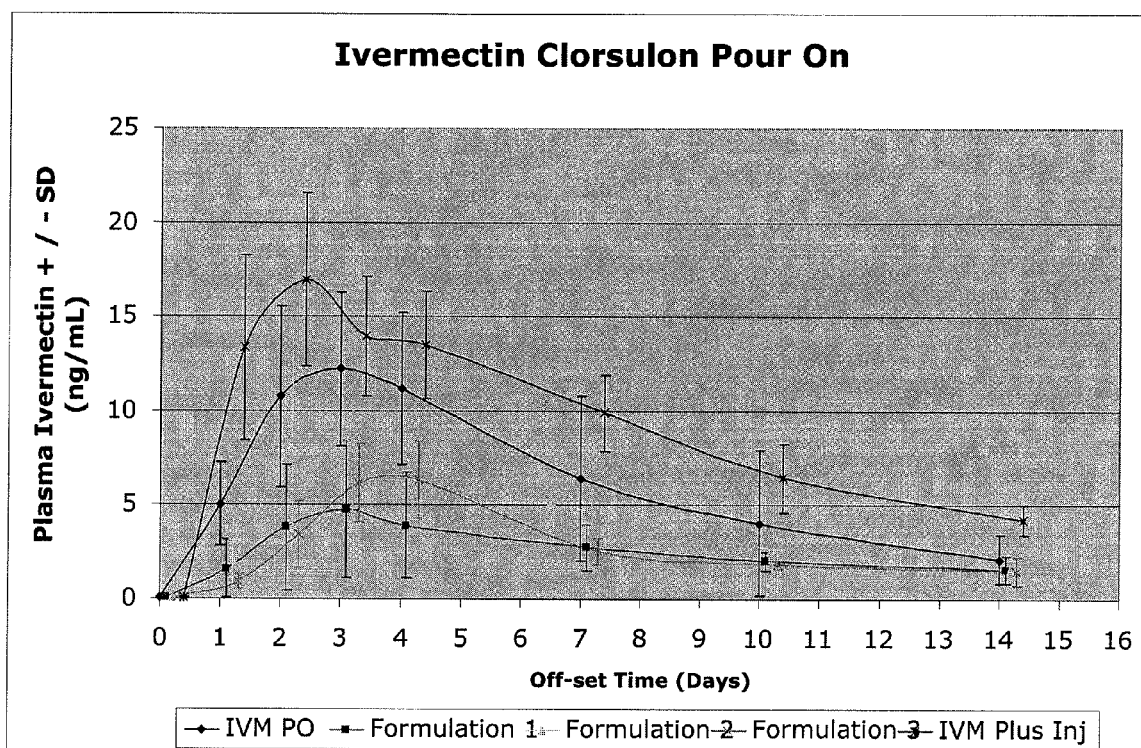
FIG. 4 is a graph depicting ivermectin plasma levels over time.
Figure 5:
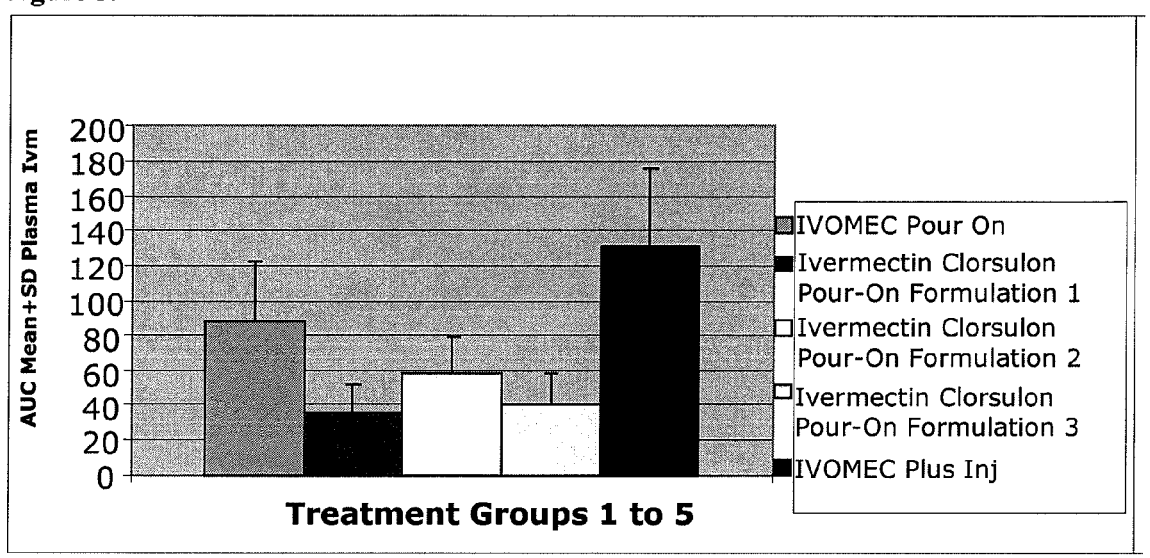
FIG. 5 is a bar graph depicting mean plasma ivermectin levels in various treatment groups.

Pharmacokinetic data pertaining to ivermectin are presented in FIGS. 4-5. The bioavailability of the ivermectin may be increased by increasing the amount of ivermectin in the inventive formulation, for example, by doubling the amount of ivermectin from 0.5% w/v to about 1.0% w/v. In other embodiments, the bioavailability of the ivermectin may be increased by increasing the amount to about 0.75% w/v.

Pharmacokinetic data were also generated with the eprinomectin formulations detailed in Table 8. These data are presented in FIGS. 6-7. When increased to about 1.0% w/v, the observed mean plasma eprinomectin AUC (D0 to 14) was higher for the Group 2 formulation (1% w/v eprinomectin) in comparison to EPRINEX PO (0.5% eprinomectin), the commercial pour-on formulation. These results demonstrate that by increasing the concentration of the macrolide, in this instance eprinomectin concentrations to about 1.0% w/v, bioavailability of the macrolide (eprinomectin in these results) may be increased. As with ivermectin discussed above, the bioavailability of the eprinomectin may thus be increased by increasing the amount of eprinomectin in the inventive formulation, for example, by doubling the amount as was done in Formulation 1 used in the pharmacokinetic studies, which results are presented in FIGS. 6-7. In other embodiments, the bioavailability of the eprinomectin may be increased by increasing the amount to about 0.75% w/v.

Example 4

Therapeutic Efficacy Against Adult Liver Flukes in Cattle

A study was conducted to evaluate the efficacy against induced infections of mature *Fasciola hepatica* and adult gastrointestinal nematodes in cattle treated (Day 0) with an eprinomectin (1% w/v) plus clorsulon (10% w/v) topical formulation. Eighteen healthy Braunvieh cattle aged between 6 to 12 months and weighing 200 to 300 kg were used. Animals were free of nematodes and fluke prior to induction of experimental infections as follows:

TABLE 14

| Species | Number of Infective Larvae | Day of Inoculation |
|---|---|---|
| *Fasciola hepatica* | 400-500 | −98 |
| *Trichostrongylus axei* | 10,000-20,000 | −21 |
| *Cooperia punctata* | 10,000-20,000 | −28 |
| *Cooperia oncophora/surnabada* | 10,000-20,000 | −21 |
| *Nematodirus helvetianus* | 3,000-5,000 | −28 |
| *Ostertagia ostertagi/lyrata* | 10,000-20,000 | −28 |

Animals were randomly allocated to either an unmedicated control group or the treated group (1 mL/10 kg body weight) based on a ranking on pre-treatment body weight.

Plasma was collected for analysis of eprinomectin and clorsulon concentrations on Days −1, 1, 2, 3, 4, 7, 10, 14, and 21. These results are presented in FIGS. 8-9.

Animals were sacrificed on Day 21 for parasite recovery (liver: total Fasciola counts; abomasum: 10% aliquot; abomasum soak: 10% aliquot; small intestine: 10% aliquot).

RESULTS: Fluke Counts 21 days after treatment (if applicable)

TABLE 15

| Group | Replicate | *Fasciola hepatica* |
|---|---|---|
| 1 | 1 | 166 |
| Control, | 2 | 223 |
| unmedicated | 3 | 50 |
| | 4 | 47 |
| | 5 | 76 |
| | 6 | 57 |
| | 7 | 29 |
| | 8 | 127 |
| | 9 | 159 |
| Geometric Mean | | 84.77 |
| 2 | 1 | 0 |
| Eprinomectin 1% w/v | 2 | 0 |
| Clorsulon 10% w/v | 3 | 0 |
| 1 mL/10 kg bodyweight | 4 | 2 |

TABLE 15-continued

| Group | Replicate | Fasciola hepatica |
|---|---|---|
| topically once on Day 0 | 5 | 0 |
|  | 6 | 0 |
|  | 7 | 0 |
|  | 8 | 0 |
|  | 9 | 1 |
| Geometric Mean |  | 0.22 |
| Efficacy |  | 99.74% |

These results provide an example of a formulation according to the invention that when topically applied to cattle infected with nematodes and liver flukes surprisingly provides adequate levels of both active agents sufficient to control these parasites. The formulation is not only stable, but also provides a useful and convenient topical dosage which, when applied as a pour-on to the backs of cattle, provides adequate plasma levels of two chemically distinct compounds to control a range of endoparasites, including trematodes and nematodes.

The above description of the invention is intended to be illustrative and not limiting. Various changes or modifications in the embodiments described herein may occur to those skilled in the art. These can be made without departing from the scope and spirit of the invention.

TABLE 5

Ivermectin and Clorsulon PK Efficacy Study Sample Stability

| Formulation # | Storage Condition | Ivermectin % w/v ||||| Clorsulon % w/v |||||
|---|---|---|---|---|---|---|---|---|---|---|---|
|  |  | Initial | 1 Month | 2 Months | 3 Months | % Change | Initial | 1 Month | 2 Months | 3 Months | % Change |
| 1 | 30° C. | 0.496 | 0.489 | 0.490 | 0.492 | 0.2 | 17.36 | 17.15 | 17.32 | 17.35 | −0.1 |
|  | 40° C. |  | 0.488 | 0.495 | 0.490 | −1.2 |  | 17.46 | 17.46 | 17.55 | 1.1 |
|  | 50° C. |  | 0.490 | 0.495 | 0.491 | −1.0 |  | 17.63 | 17.57 | 17.65 | 1.6 |
| 2 | 30° C. | 0.500 | 0.494 | 0.472 | 0.492 | −1.6 | 17.47 | 17.54 | 17.35 | 17.43 | −0.2 |
|  | 40° C. |  | 0.492 | 0.499 | 0.494 | −1.2 |  | 17.56 | 17.56 | 17.57 | 0.6 |
|  | 50° C. |  | 0.497 | 0.498 | 0.492 | −1.6 |  | 17.02 | 17.51 | 17.96 | 2.8 |
| 3 | 30° C. | 0.500 | 0.489 | 0.501 | 0.491 | −1.8 | 17.21 | 16.73 | 17.46 | 17.43 | 1.3 |
|  | 40° C. |  | 0.485 | 0.494 | 0.490 | −2.0 |  | 17.21 | 17.66 | 17.40 | 1.1 |
|  | 50° C. |  | 0.493 | 0.497 | 0.499 | −0.2 |  | 16.84 | 17.76 | 17.61 | 2.3 |

TABLE 6

Various formulations of active agent (as indicated) in Miglyol 840, Glycerol Formal and Glycol Ethers (% v/v)

| Sample | Clorsulon (% w/v) | Ivermectin (% w/v) | Carbitol | Glycerol Formal | Miglyol 840 | Arcosolve | PEG 200 | PPG |
|---|---|---|---|---|---|---|---|---|
| 1 | — |  | 35 | 70 | 5 | 25 | — | — |
| 2 | — |  | 17.5 | 70 | 5 | 25 | — | — |
| 3 | — |  | 35 | 64 | 4.8 | 31 | — | — |
| 4 | — |  | 35 | 47 | 3.1 | 50 | — | — |
| 5 | — |  | 32 | 50 | 2.9 | 46 | — | — |
| 6 | — |  | 15 | 32 | 35.3 | 34 | — | — |
| 7 | — |  | 35 | 55 | 5 | 40 | — | — |
| 8 | — |  | 35 | — | 5 | 50 | 45 | — |
| 9 | 1 |  | 35 | 65 | 5 | 30 | — | — |
| 10 | 1 |  | 35 | 65 | 10 | 25 | — | — |
| 11 | — |  | 35 | — | 5 | 30 | 65 | — |
| 12 | — |  | 32 | 50 | 4.5 | 36 | — | 9 |
| 13 | — |  | 32 | 50 | 4.5 | 36 | 9 | — |
| 14 | — |  | 35 | 75 | 5 | 20 | — | — |
| 15 | — |  | 35 | 70 | — | 25 | 5 | — |
| 16 | 1 |  | 35 | — | — | 25 | 70 | 5 |
| 17 | 0.5 |  | 17.5 | 70 | 5 | 25 | — | — |
| 18 | 0.5 |  | 17.5 | 70 | 5 | 25 | — | — |
| 19 | 0.5 |  | 17.5 | — | 5 | 30 | 65 | — |
| 20 | 0.5 |  | 17.5 | — | 5 | 30 | 65 | — |
| 21 | 0.5 |  | 17.5 | — | — | 25 | 70 | 5 |
| 22 | 0.5 |  | 17.5 | 75 | — | 25 | — | — |
| 23 | 0.5 |  | 17.5 | 75 | — | 25 | — | — |

TABLE 6-continued

Various formulations of active agent (as indicated) in Miglyol 840, Glycerol Formal and Glycol Ethers (% v/v)

| | Eprinomectin (% w/v) | | | | | | | |
|---|---|---|---|---|---|---|---|---|
| 24 | 0.5 | 17.5 | 70 | 5 | 25 | — | — | — |
| 25 | 0.5 | 17.5 | — | 5 | 30 | 65 | — | — |

| Sample | Ivermectin (% w/v) | Clorsulon (% w/v) | IPA | Glycerol Formal | CAP | TEA |
|---|---|---|---|---|---|---|
| 26 | 0.5 | 17.5 | 70 | 5 | 25 | — |

PPG = Propylene Glycol,
PEG = Polyethylene Glycol
IPA = Isopropyl Alcohol,
TEA = Triethylamine,
CAP = Cetostearyl Ethylhexanoate & Isopropyl Myristate proprietary ingredient.

TABLE 7

Ivermectin and Clorsulon Formulation Examples

| Formulation Number | Treatment Group | Clorsulon (% w/v) | Ivermectin (% w/v) | Carbitol (% w/v) | Arcosolv (% w/v) | Glycerol Formal (% w/v) | Miglyol 840 (% w/v) | IPA (% w/v) | Crodamol CAP (% w/v) | TEA (% w/v) |
|---|---|---|---|---|---|---|---|---|---|---|
| 1 | Group 2 | 17.5 | 0.5 | 70 | — | 5 | 25 | — | — | — |
| 2 | Group 3 | 17.5 | 0.5 | — | 65 | 5 | 30 | — | — | — |
| 3 (Control Formulation, similar to: IVOMEC Pour-On formulation) | Group 4 | 17.5 | 0.5 | — | — | 15 | — | 65 | 15 | 0.05 |

Transcutol (Methyl) Carbitol = Diethylene glycol monoethyl ether
Arcosolv DPM = Dipropylene glycol monomethyl ether
TEA = Triethanolamine
IPA = isopropanol
Miglyol 840 = propylene glycol dicaprylate/dicaprate

TABLE 8

Eprinomectin and Clorsulon Formulation Examples

| Formulation Number | Treatment Group | Clorsulon (% w/v) | Eprinomectin (% w/v) | Carbitol (% w/v) | Glycerol Formal (% w/v) | Miglyol 840 (% w/v) | BHT (% w/v) |
|---|---|---|---|---|---|---|---|
| 1 | Treatment Group 2 | 10 | 1.0 | 40 | 5 | 43 | 0.05 |
| 2 | Treatment Group 3 | 10 | 0.5 | 58 | 5 | 25 | 0.05 |
| 3 | Treatment Group 4 | 10 | 0.5 | 40 | 5 | 43 | 0.05 |

TABLE 9

Eprinomectin and Clorsulon PK Sample Stability

| | | Eprinomectin % w/v | | | | | Clorsulon % w/v | | | | |
|---|---|---|---|---|---|---|---|---|---|---|---|
| Formulation # | Storage Conditions | Initial | 1 Month | 2 Month | 3 Month | % Change | Initial | 1 Month | 2 Month | 3 Month | % Change |
| 1 | 30° C. | 1.013 | 1.007 | 1.014 | 0.999 | −1.38 | 9.92 | 9.82 | 9.86 | 9.89 | −0.30 |
| | 40° C. | | 1.008 | 1.008 | 1.011 | −0.20 | | 9.88 | 9.92 | 9.83 | −0.91 |
| | 50° C. | | 1.012 | 1.018 | 1.001 | −1.18 | | 9.86 | 9.91 | 9.95 | 0.30 |
| 2 | 30° C. | 0.517 | 0.521 | 0.519 | 0.521 | 0.77 | 10.04 | 10.26 | 9.82 | 10.03 | −0.10 |
| | 40° C. | | 0.520 | 0.518 | 0.517 | 0.00 | | 10.29 | 10.19 | 10.21 | 1.69 |
| | 50° C. | | 0.519 | 0.521 | 0.517 | 0.00 | | 10.30 | 10.16 | 10.07 | 0.30 |

TABLE 9-continued

Eprinomectin and Clorsulon PK Sample Stability

| Formulation # | Storage Conditions | Eprinomectin % w/v | | | | | Clorsulon % w/v | | | | |
|---|---|---|---|---|---|---|---|---|---|---|---|
| | | Initial | 1 Month | 2 Month | 3 Month | % Change | Initial | 1 Month | 2 Month | 3 Month | % Change |
| 3 | 30° C. | 0.510 | 0.507 | 0.509 | 0.505 | −0.98 | 9.87 | 9.96 | 9.92 | 9.93 | −0.41 |
| | 40° C. | | 0.507 | 0.506 | 0.505 | −0.98 | | 9.97 | 9.89 | 9.97 | 1.01 |
| | 50° C. | | 0.504 | 0.509 | 0.507 | −0.59 | | 9.99 | 9.98 | 10.00 | 1.32 |

What is claimed is:

1. A stable veterinary formulation for topical, transdermal treatment or prophylaxis of a parasitic infection or infestation in an animal, comprising:
   (a) about 8% to about 12% (w/v) clorsulon;
   (b) about 0.3% to about 2% (w/v) eprinomectin;
   (c) about 40% to about 60% diethylene glycol monoethyl ether;
   (d) about 5% glycerol formal;
   (e) about 20% to about 50% (w/v) propylene glycol diesters of caprylic and capric acids; and
   (f) from zero to about 0.1% (w/v) butylated hydroxy toluene.

2. The formulation of claim 1 comprising:
   (a) about 10% (w/v) clorsulon;
   (b) about 0.5% (w/v) or about 1.0% (w/v) eprinomectin;
   (c) about 40% or about 58% diethylene glycol monoethyl ether;
   (d) about 5% glycerol formal;
   (e) about 25% or about 43% (w/v) propylene glycol diesters of caprylic and capric acids; and
   (f) about 0.05% (w/v) butylated hydroxy toluene.

3. The formulation of claim 1 or 2 wherein the stability of the macrocyclic lactone active agent is enhanced in that less than 20% by weight of macrocyclic lactone degradation is demonstrated when the formulation is stored at 50° C. for three months.

4. A method of treating or preventing parasitic infection in an animal, comprising topically administering the formulation of claim 1, 2, or 3 to the animal.

* * * * *